United States Patent [19]

Holloway et al.

[11] Patent Number: 5,070,158

[45] Date of Patent: Dec. 3, 1991

[54] COVALENTLY LABELED SILOXANE POLYMERS

[75] Inventors: Robert R. Holloway, Montara; Teddy T. Kiang, Sunnyvale, both of Calif.

[73] Assignee: Hewlett-Packard Company, Palo Alto, Calif.

[21] Appl. No.: 274,626

[22] Filed: Nov. 22, 1988

Related U.S. Application Data

[63] Continuation-in-part of Ser. No. 24,940, Mar. 12, 1987, abandoned.

[51] Int. Cl.⁵ .............................................. C08G 77/22
[52] U.S. Cl. ...................................... 525/475; 528/30; 528/34; 528/43; 546/10; 546/14
[58] Field of Search .................. 528/24, 30, 43, 37, 528/34, 30, 43, 33; 525/475; 546/10, 14

[56] References Cited

U.S. PATENT DOCUMENTS

| | | | |
|---|---|---|---|
| 3,036,035 | 5/1962 | Riley | 528/33 |
| 3,169,942 | 2/1965 | Pike | 528/34 |
| 3,269,981 | 8/1966 | Goossens | 528/34 |
| 3,383,355 | 5/1968 | Cooper | 528/43 |
| 4,194,877 | 3/1980 | Peterson | 8/4 |
| 4,468,229 | 8/1984 | Su | 8/507 |
| 4,712,865 | 12/1987 | Hsu et al. | 350/96.29 |

FOREIGN PATENT DOCUMENTS

| | | |
|---|---|---|
| 0274184 | 7/1988 | European Pat. Off. . |
| 2018797 | 10/1979 | United Kingdom . |
| 2018804 | 10/1979 | United Kingdom . |
| 2132348 | 7/1984 | United Kingdom . |

OTHER PUBLICATIONS

"Chemistry and Technology of Silicones", Walter Noll, Academic Press, 1968, pp. 395–399.
Petrarch Systems Catalogue, Bristol, PA, pp. 176, 182–184, 186, 188.
"Energy Transfer from Luminescent Transition Metal Complexes to Oxygen", Journal of the American Chemical Society, vol. 99, Number 11, May 25, 1977, pp. 3547–3551.
Hirsch et al., "Silicon-containing Dyes", *Chemical Abstracts*, vol. 97, No. 16, Oct. 1982, Abstract 129108y, p. 82.

*Primary Examiner*—John C. Bleutge
*Assistant Examiner*—R. Dean, Jr.
*Attorney, Agent, or Firm*—Frank R. Perillo

[57] ABSTRACT

Disclosed herein is a method of labeling room temperature vulcanizable silicon polymers at the "T" junction branch points by utilizing cross-linkers of the formula D-SiX₃, wherein X is a leaving group and D is a complex organic molecule useful as a dye, fluorophore, or indicator.

7 Claims, 1 Drawing Sheet

COVALENTLY LABELED SILOXANE POLYMERS

CROSS REFERENCE TO RELATED APPLICATION

This application is a continuation-in-part of application Ser. No. 07/024,940, filed Mar. 12, 1987, now abandoned.

TECHNICAL FIELD

The invention relates to silanol-terminated polymers which are formed from bifunctional organosilicon, and cross-linked with trifunctional silane. More specifically, it relates to siloxane polymers containing covalently bound dyes, fluorophores, or other complex organic moieties at the junction points occupied by the cross-linker.

BACKGROUND ART

Organic silicone polymers are useful in a variety of applications. A group of these materials, silicone polymers formed using trifunctional silanes as cross-linkers, have multiple T-junctions. These polymers are, when properly derivatized, used as the bases for polishes, water repellant coatings for fabrics, and contact lens materials. A subset of these materials is known as RTVs (room temperature vulcanizable) polymers. (It is also possible to cross-link basic polymers formed from bifunctional silane to obtain X branches through the use of tetrafunctional silane compounds.)

In some applications, it is desirable to include, in the polymer, materials which will serve a labeling or indicating function, or which will simply color the material as in the case of colored contact lens materials. For example, U.K. Patent Application 2,132,348A discloses a method and apparatus for determining the presence of oxygen which employs a sensor material embedded in a silicone resin. The resin is impermeable to quenchers other than the oxygen analyte, which interfere with the determination, and thus offers an advantage over use of the sensing material directly. Similar materials are available for the detection and quantitation of other atmospheric components such as carbon dioxide or for measurement of, for example, pH or other specific analytes.

The present systems which employ silicone polymer supports for the detecting or coloring material suffer from the disadvantage that the reagent is not covalently bound to the polymer and therefore is both difficult to control as to concentration and is subject to instability and leakage. One approach to solving these problems is to link the detecting or other desired material covalently to the polymer support.

Others have applied this general approach using different, non-silicone, polymeric backbones. For example, U.S. Pat. No. 4,194,877 to Peterson discloses the preparation of a dye/acrylic copolymer as a pH sensor. Similarly, U.S. Pat. No. 4,468,229 discloses contact lens compositions wherein reactive dye materials are covalently bound to the monomeric starting materials which are then polymerized. In this case, the resulting polymer is basically a highly substituted polyethylene backbone; that is, for example, the basic polymer is of a hydroxyalkyl ester of an unsaturated acid, most commonly hydroxyethyl methacrylate. Applicants are unaware of any general method of binding indicator reagents or other desired complex reactive materials covalently to silicone polymers.

Since the properties of silicone polymers are advantageous in many applications, it would be useful to have available the corresponding covalently labeled materials having silicone backbones. The present invention provides such methods and materials.

DISCLOSURE OF THE INVENTION

The invention provides labeled silicone polymers which are resistant to leakage of the label from the matrix and which permit control of the quantity of label present. The labels may be sensing reagents, dyes, fluorophores, or other materials which provide optical properties to the polymer or which provide specific reagents for detection of analytes. The desired complex derivatives are supplied in the form of cross-linking trifunctional silanes of the formula D—SiX$_3$, wherein D is the derivatizing dye or fluorophore, and X is a leaving group responsive to the [—Si—O—] attacking nucleophile.

Accordingly, in one aspect, the invention is directed to silicone polymers containing organic dyes or fluorophores covalently bonded to the T-junctions. A particularly preferred group of dyes and fluorophores are the polyaromatic salts of heavy metal ions. The invention in other aspects also relates to methods of preparing these derivatized polymers and to intermediaries in their preparation, including compounds of the formula D—SiX$_3$, wherein X is a leaving group most conveniently selected from halo, acyloxy, amine, oxime and alkoxy. In still other aspects, the invention relates to methods to use the resulting derivatized polymers.

Figure 1:
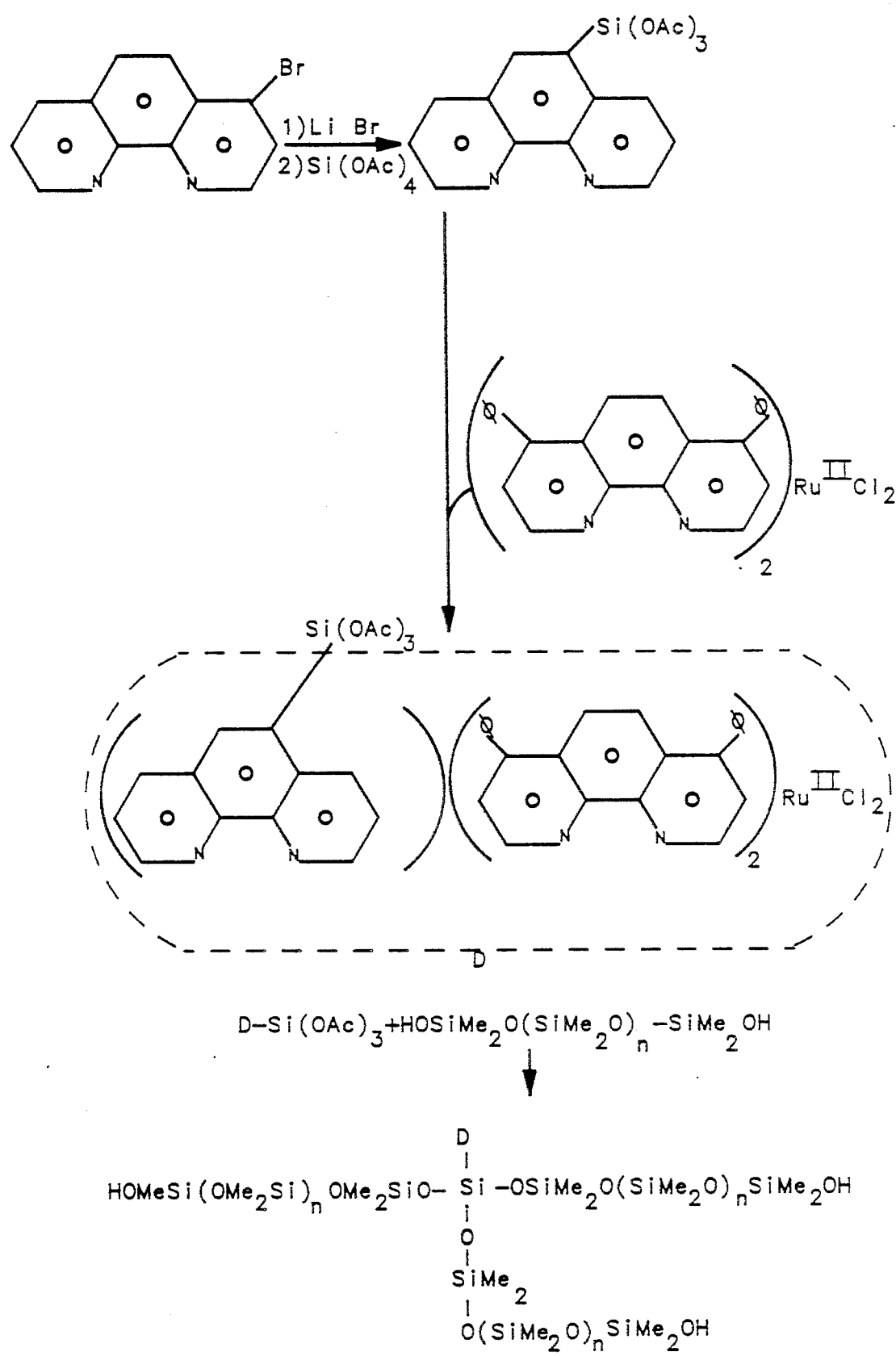
FIG. 1 is a schematic indicating the derivatization of the cross-linked silicone rubbers of the invention.

MODES OF CARRYING OUT THE INVENTION
DEFINITIONS

As used herein, "complex organic moiety" refers to an organic radical which is a dye, fluorophore, or indicator for an analyte. Specifically excluded are simple alkyl and phenyl radicals, when those contain only one or two functional groups which do not result in the capability of the radical to absorb or emit visible light, either when bound alone to the polymer or in the presence of a specific non-absorbing or emitting analyte, or both.

Examples of such "complex organic moieties" include acid-base indicators, such as phenolphthaleins, phenol sulfonphthaleins, aniline sulfonphthaleins, benzeins, and various mixed indicators; fluorescent indicators, such as fluorescein, and chemiluminescent indicators; metal ion indicators, such as azo dyes, alizarins, and triphenylmethanes; and redox indicators, such as azines, methylene blue and other thiazines, viologens, oxazines, variamine blues, indigo sulfonic acids, indophenols, indoanilines and indamines, the diphenylamine-diphenylbenzidine series, diimine iron (II) chelates, diimine ruthenium (II) chelates, diimine osmium (II) chelates, diimine iridium (III) chelates, and various mixed, fluorescent, and chemiluminescent indicators. Further examples of these organic substituents include dyes for coloration, scintillators (radiation indicators) such as the POPOP's; antioxidants and oxygen scavengers, such as DABCO, BHA, BHT and the cyclohexadienes; and indicators for specific toxic compounds, such as oxazines and certain fluorescent indicators.

"Junction" refers to the Si atom contributed by the trifunctional silane cross-linker in obtaining "T" linked silane-terminated single chain dialkyl siloxane polymers, as further described below. Thus, complex organic moieties attached to the "junction" refer to those covalently bonded to this silicon.

THE SILICONE AND THE COMPLEX ORGANIC LIGAND

The invention is directed to a method of attaching complex organic moieties to T-junction containing silicone polymers, including room temperature vulcanizable (RTV) silicone polymers. As a class, these polymers are formed by cross-linking silanol-terminated polydialkyl siloxane, in particular, polydimethyl siloxane, with a trifunctional derivatized silane containing the complex moiety desired to be included in the finished cross-linked polymer. In general, these systems are formulated using single chain polymers of molecular weight 26 kd-200 kd of the general formula conventionally written in the form of formula (1) for the most common type, the dimethyl:

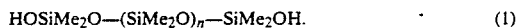

$$HOSiMe_2O—(SiMe_2O)_n—SiMe_2OH. \quad (1)$$

For the polydimethyl siloxane polymers, the nomenclature is often abbreviated to PDM. The generic dialkyl analogs contain alkyl groups of 1-5 carbons, which are straight or branched chains. The polymers which contain alkyl groups other than methyl are, however, relatively less economical and offer no particular advantage in the compositions of the invention.

To obtain the T-junction-containing forms, the single chain polymers are then cross-linked as shown in FIG. 1 using a compound of the general formula

$$R—SiX_3 \quad (2)$$

wherein X is a suitable leaving group and R is either methyl or a simple organic substituent such as, for example, aminoalkyl, carboxypropyl, glycidoxypropyl, phenylethylsulfonate, or vinyl. The cross-linker reacts with the PDM or other polydialkyl siloxanes by virtue of a putative nucleophilic attack on the silicon center of the cross-linker by the partially ionized hydroxy groups contained on the silanol-terminating entities in the straight chain polymers, thus forming a series of T-junctions when all three leaving groups of the R—SiX$_3$ cross-linker have been displaced. The mechanism of this reaction is not at present precisely understood, but it is known that the nature of X must be that of a group capable of heterolytic cleavage from Si of the form Si+:X.

It is evident, therefore, that the end product will contain the substituent designated "R" at the silicon atom occupying the crossbar of the T junctions brought in by the cross-linker, as illustrated in FIG. 1.

In the present invention, R, rather than being a simple side chain such as methyl or the derivatives mentioned above, is a complex organic molecule such as a dye or a fluorophore which is capable of an indicating functionality. The cross-linker, therefore, has the formula

D—SiX$_3$ wherein D- can be chosen from a variety of complex substances as set forth above including heavy metal-containing sensors useful in determination of oxygen, dyes useful in coloring contact lens compositions, and fluorophores useful in tagging polymers used for various purposes to make them easy to detect.

Also included among the dyes and fluorophores which may be supplied according to the method of the invention are included fluorophores such as fluorescein and dansyl groups, dyes such as phenol red, methylene blue, alazarine yellow, a variety of azo dyes, and heavy metal containing dyes such as aromatic complexes of ruthenium (II), osmium (II) and iridium (II).

PREPARATION AND REACTION OF THE DERIVATIZED CROSS-LINKER

The cross-linking moiety of the invention is prepared by linking the desired organic molecule to a tetrafunctional silane of the formula SiX$_4$ wherein X is the leaving group as set forth above, i.e., capable of displacement by the silanol end groups in PDM in the formation of a silicon oxygen bond. The general scheme is shown in FIG. 1. Thus, X is generally any suitable electron withdrawing group capable of displacement from Si, most conveniently acyloxy. (Acyloxy is defined as a group of the formula RCOO—, wherein R is an alkyl of 1-5 carbon atoms, such as acetyl, propionyl, butanoyl, and the like).

Other embodiments of X may also be used. Commonly known in the art of leaving groups are halo (particularly chloro) or amino (particularly dimethylamino), oximato or alkoxy (RO—) wherein R is alkyl as above defined. Certain of these leaving groups require a catalyst for reaction with the silanol-terminated polymer single chains; for example the reaction of alkoxy derivatized cross-linkers is catalyzed by titanates and carboxylic acid salts of zinc, iron and tin as is generally known in the art.

The novel cross-linking agents of the invention are therefore obtained by reaction of the compound of the formula SiX$_4$ with a modification of the complex organic moiety, D-, which has been modified in such manner that the organic radical D- behaves as a nucleophile. Typically such modification will take the form of a Grignard reagent containing a carbon to metal bond between D- and a metal such as lithium, magnesium, or sodium, or between a precursor of D- and such metals. Such Grignard complexes can be formed using functionalities present in the dyes such as halo moieties, unsaturation, and so forth according to means generally known in the art. In theory, this Grignard reagent may also be formed with a portion of or a precursor to D-, and the complete conjugate obtained by reaction subsequent to attachment of the portion to the cross-linker, or even after the cross-linking reaction itself. Indeed, in a preferred embodiment set forth below, the diphenyl-phenanthroline attached to the trifunctional silane cross-linker is covalently bonded first to the silicon, and the complete 1,10-phenanthrolyl-bis (4,7-diphenyl-1,10-phenanthrolyl) ruthenium II chloride is formed using the already bound component. However, preparation of particularly preferred polyphenanthroline derivatives of heavy metals, such as a derivatized silicone rubber matrix covalently bound to a tri (phenanthroline) heavy metal dye, has been found to require the use of a particular solvent system and preparation pathway. This will be more specifically described below.

METHOD OF USE

A particularly useful series of organic dyes and photosensitizers is described in Demas, J. N. et al, *J Chem*

Soc (1977) 99:3547-3551, incorporated herein by reference. These compounds are generally polyphenanthroline derivatives of heavy metals. The use of these complexes in detection of oxygen is described in the above-referenced British patent published application 2,132,348A, also incorporated herein by reference. Briefly, the fluid to be tested for oxygen is passed into contact with a silicone polymer containing the photosensitive fluorescent indicating moiety physically trapped in the matrix, but not covalently bound to it. The fluorescent light emitted by the indicating moiety under excitation is measured. The oxygen contained in the test solution is capable of quenching the light emission and thus the reduction in light emission observed and measured when the matrix is in contact with the test sample is proportional to the concentration of oxygen in the test sample. The method of the invention represents an improvement over this general method in that the photosensitized sensor is covalently attached to the embedding surface and not susceptible to leakage into the solution or suspension to be assayed.

PREFERRED EMBODIMENTS

In one particularly preferred embodiment, a derivatized silicone rubber matrix covalently bound to a tri (phenanthroline) ruthenium (II) dye is prepared by reaction of silicon tetraacetate with 5-phenanthrolyl lithium. The resulting 5-(triacetoxysilyl) phenanthroline is then reacted with bis (diphenylphenanthroline) ruthenium (II) dichloride to obtain the desired derivatized cross-linker. This reaction of the 5-(triacetoxysilyl)-phenanthroline as a precursor with bis (diphenyl-phenanthroline) ruthenium (II) dichloride (and for other heavy metal containing dyes such as aromatic complexes of osmium (II) and iridium (III)) must be conducted in a polar solvent system that is free of water.

More particularly, the polar solvent system should include two components: one component removes, or binds, water, and preferably is an active metal or the anhydride of the other component; the other component avoids problems from the self-reactivity of the cross-linker, and preferably is the conjugate base of the alcohol (with reference to X as acyloxy or alkoxy) or is the anhydride. For example, for D'-Si[OR']$_3$ when R' is acyl, then the solvent system would be HOR' and (R')$_2$O. For D'—Si[OR']$_3$ when R' is alkyl, then the solvent system would be HOR, and an active metal.

In more detail, 5-bromophenanthroline is reacted with n-butyl lithium to obtain the modified phenanthroline nucleus with lithium replacing bromo in the 5 position and converting the tricyclic ring system into a nucleophile. The thus modified phenanthroline is then reacted with silicon tetraacetate to obtain 5-triacetoxy silyl phenanthroline (an example of D'-Si[OR']$_3$), which is then reacted in a solvent system such as glacial acetic acid/acetic anhydride with bis (diphenylphenanthroline) ruthenium (II) dichloride (to complete the polyaromatic moiety of D' and to add the heavy metal salt).

The product of the formula (3)

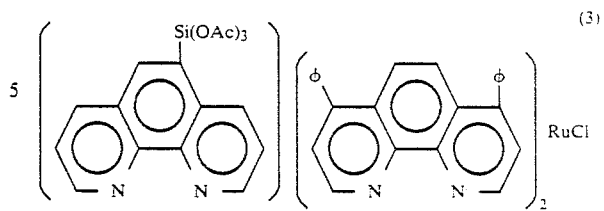

is then used as a cross-linker to form the desired polymer, carrying with it the tri diphenanthroline ruthenium moiety, 1,10-phenanthrolyl-bis (4,7-diphenyl-1,10-phenanthrolyl) ruthenium (II) chloride.

The cross-linker is reacted with a preparation of single chain polymeric silanol-terminated polydialkyl silane, such as with 18,000 ctsk silanol end-capped polydimethylsilane, using dibutyl tin dilaurate as a catalyst, as is generally understood in the art.

EXAMPLES

The following examples are intended to illustrate but not to limit the invention.

EXAMPLE 1

Preparation of 5-Triacetoxysilyl Phenanthroline

In a dry, oxygenless system, 0.025 g 5-bromophenanthroline is dissolved in 10 ml dry, peroxide-free tetrahydrofuran. 0.15 ml butyl lithium (1.6 M in toluene) solution is added with stirring. After five minutes, the contents of the reaction flask are transferred to another dry, oxygenless container in which 0.3 g silicon tetraacetate is dissolved in 10 ml dry, peroxide-free tetrahydrofuran. The silyl phenanthroline, along with the considerable excess of silicon tetraacetate, are suitable for preparation of the dye cross-linker (Example 2).

EXAMPLE 2

Preparation of Dye Cross-Linker

Samples containing 0.040 g 5-triacetoxysilyl phenanthroline and 0.08 g cis-dichloro-bis-diphenyl phenanthrolyl ruthenium (II) are combined with 10 ml 1:1 glacial acetic acid/acetic anhydride solution under an inert, dry gas and stirred at 40 C for twenty-four hours.

EXAMPLE 3

Preparation of Cross-linked Labeled Polymer

Polydimethylsiloxane-bound
Phenanthrolyl-bis-diphenyl-phenanthrolyl Ruthenium (II)

5 g of silanol-capped polydimethylsiloxane, molecular weight 77,000 is dissolved in 50 ml chloroform. 0.3 grams of silicon tetraacetate or methyl triacetoxysilane containing the desired amount of dye cross-linker and two drops of dibutyl tin dilaurate are rapidly beat into the chloroform solution with a blender. The solvent is then removed with a rotary evaporator. Curing is complete in a day.

It is claimed:
1. A method to derivatize silicone polymers by incorporating therein heavy metal ion polycyclic-aromatic salts, which comprises:
reacting silanol-terminated single-chain dialkyl siloxane polymers with a cross-linker of the formula D—SiX$_3$ wherein D is a heavy metal ion polycyclic-aromatic salt, and X is a leaving group.

2. The method as in claim 1 wherein the cross-linker is the product of a chemical reaction in a polar solvent.

3. The method as in claim 2 wherein X is represented as (OR'), with R' being acyl or alkyl, the cross-linker is formed from a precursor having the formula D'—Si(OR')$_3$, wherein D' is a complex organic or organometallic substituent, and the polar solvent is HOR' and (R')$_2$O where R' is acyl or HOR' and an active metal when R' is alkyl.

4. The method of claim 1 wherein X is selected from the group consisting of acyloxy, alkoxy, oxime, amine, and halo.

5. The method of claim 1 wherein D is an acid-base indicator, a fluorescent indicator, a chemiluminescent indicator, a metal ion indicator, a redox indicator, a dye indicator, a scintillator, or an oxygen scavenger.

6. The method of claim 1 wherein D is a ruthenium II complex.

7. The method of claim 6 wherein D is 1,10-phenanthrolyl-bis (4,7-diphenyl-1,10-phenanthrolyl) ruthenium II chloride.

* * * * *